United States Patent [19]

Brunelle et al.

[11] Patent Number: 4,994,595

[45] Date of Patent: Feb. 19, 1991

[54] PREPARATION OF SPIROBIINDANE BISPHENOL BISCHLOROFORMATE COMPOSITIONS

[75] Inventors: Daniel J. Brunelle, Scotia; Thomas G. Shannon, Schenectady, both of N.Y.

[73] Assignee: General Electric Company, Schenectady, N.Y.

[21] Appl. No.: 926,685

[22] Filed: Nov. 4, 1986

[51] Int. Cl.$^5$ .................. C07C 68/02; C07C 69/96
[52] U.S. Cl. .................................. 558/281; 558/282
[58] Field of Search ................... 558/281, 282, 280

[56] References Cited

U.S. PATENT DOCUMENTS 4,601,858  7/1986  Shannon et al. ............... 558/281
4,638,077  1/1987  Brunelle et al. ............... 558/281

FOREIGN PATENT DOCUMENTS 8603192  11/1985  PCT Int'l Appl. .

Primary Examiner—Vivian Garner
Attorney, Agent, or Firm—William H. Pittman; James C. Davis, Jr.

[57] ABSTRACT

Bischloroformate compositions are prepared from spirobiindane bisphenols by phosgenation in a substantially inert organic liquid in a two-step reaction. The pH during the first step is maintained in the range of about 8–14 by addition of aqueous base. In the second step, the pH is in the range of about 2–6. This method produces compositions containing a substantial amount of monomeric bischloroformate and avoids gelling problems.

11 Claims, No Drawings

PREPARATION OF SPIROBIINDANE BISCHLOROFORMATE COMPOSITIONS

This invention relates to the preparation of bischloroformates of spirobiindane bisphenols.

Numerous patents have issued and patent applications have been published recently dealing with cyclic polycarbonate oligomers, which are of interest by reason of their utility in a wide variety of polymerization methods to produce linear polycarbonates. In particular, they may be used in reactive processing methods which are unemployable with any other known method of making polycarbonates. Reference is made, for example, to copending, commonly owned application Ser. No. 704,122, filed Feb. 22, 1985, now U.S. Pat. No. 4,644,053 and corresponding European patent application No. 162,379, the disclosures of which are incorporated by reference herein.

In copending, commonly owned application Ser. No. 887,503, filed July 21, 1986, now U.S. Pat. No. 4,638,071 there are specifically disclosed cyclic polycarbonate oligomers derived from 6,6'-dihydroxy-3,3,3',3'-tetramethylspirobiindanes. Such oligomers are capable of especially facile conversion to cyclic polycarbonate oligomers, and the linear polycarbonates prepared therefrom have particularly useful and interesting properties including high glass transition temperatures, which make them valuable for use in various applications.

For the most part, the cyclic polycarbonate oligomer compositions are prepared by cyclization of bisphenol bischloroformate compositions in the presence of aqueous base, a tertiary amine and a substantially inert organic liquid. The bischloroformate compositions may in turn be prepared by the reaction of the bisphenol with phosgene in the presence of aqueous base, in an organic liquid of the same type. Reference is made, for example, to copending, commonly owned application Ser. No. 790,909, filed Oct. 24, 1985, now U.S. Pat. No. 4,638,077, and corresponding PCT published application No. 86,03192, the disclosures of which are also incorporated by reference herein. In brief, those applications disclose the passage of phosgene into a mixture of said liquid and said bisphenol, with the simultaneous introduction of base to maintain a pH in the range of 0.5–8 in the aqueous phase.

Attempts to prepare spirobiindane bisphenol bischloroformates by this method have met with difficulty. The spirobiindane bisphenols swell and gel at low pH in mixtures of water and organic liquids such as methylene chloride. As a result, stirring and phosgenation are impossible, even at very low concentrations of reactants. When a similar process is conducted at high pH, the product contains relatively high levels of oligomeric chloroformates at the expense of monomer bischloroformate.

The present invention provides a method for producing spirobiindane bisphenol bischloroformate compositions containing a substantial proportion of monomer bischloroformate. Said method is simple, convenient and relatively inexpensive, and the products obtained thereby are readily cyclizable to cyclic spirobiindane polycarbonate oligomer compositions.

In its broadest sense, the invention is a method for preparing a composition comprising bischloroformates of spirobiindane bisphenols of the formula

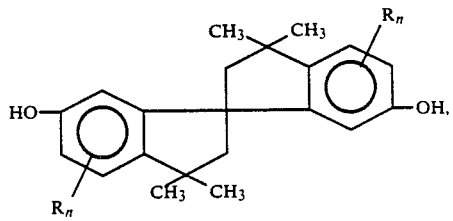

wherein each R is independently $C_{1-4}$ primary or secondary alkyl or halo and n is from 0 to 3, which comprises (A) passing phosgene into a heterogeneous mixture of said spirobiindane bisphenol, a substantially inert organic liquid and an aqueous alkali metal or alkaline earth metal base solution, said mixture being maintained at a temperature within the range of about 10°–40° C. and a pH of the aqueous phase in the range of about 8–14, until all solids have dissolved, and (B) continuing phosgene passage as the pH of the aqueous phase is decreased to a value in the range of about 2–6.

The R values in the spirobiindane bisphenols of the above formula may be alkyl radicals such as methyl, ethyl, 1-propyl or 2-propyl, or halo atoms such as chloro or bromo. Among compounds containing such R values, methyl and chloro are preferred; however, the most preferred compound is 6,6'-dihydroxy-3,3,3',3'-tetramethylspiro(bis)indane, in which n is 0. This compound is frequently identified hereinafter as "SBI".

Such spirobiindane bisphenols may in turn be prepared by the acid-catalyzed condensation of bisphenols of the formula

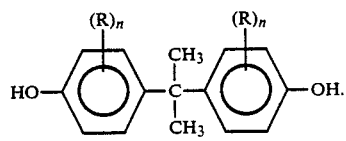

Suitable methods of preparation are disclosed, for example, in U.S. Pat. No. 3,271,463 and copending, commonly owned application Ser. No. 917,644, filed Oct. 10, 1986, now U.S. Pat. No. 4,791,234, and Ser. No. 917,645, filed Oct. 10, 1986, now U.S. Pat. No. 4,701,566.

In step A of the method of this invention, phosgene is passed into a heterogeneous mixture of the spirobiindane bisphenol, a substantially inert organic liquid and an aqueous alkali metal or alkaline earth metal base. The liquid need not dissolve substantial amounts of the spirobiindane bisphenol. However, it should be a solvent for the bischloroformate product and should generally be substantially insoluble in water. Illustrative liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

Phosgene is passed into the heterogeneous spirobiindane bisphenol-liquid mixture while said mixture is maintained at a temperature within the range of about 10°–40° C. The phosgene is ordinarily introduced in gaseous form, but its introduction as a liquid or as a solution in a suitable solvent is within the scope of this invention.

The phosgene flow rate is not critical; it is usually about 0.05–3.0 moles per equivalent of spirobiindane bisphenol per minute. (For the purposes of this invention, the equivalent weight of a spirobiindane bisphenol is its molecular weight divided by 2.)

An aqueous solution of alkali metal or alkaline earth metal base, most often a hydroxide such as sodium hydroxide, potassium hydroxide or calcium hydroxide, is added as necessary during step A to maintain a pH of the aqueous phase in the range of about 8–14. At lower pH values within this range, a substantial proportion of spirobiindane bisphenol monochloroformate may be obtained. Therefore, the preferred pH during step A is in the range of about 12–14. The concentration of the base solution is not critical and may be, for example, about 1–16N, and the proportion of base required can readily be determined by routine experimentation.

The invention is based in part on the discovery that the solubility of the reaction product increases as phosgenation proceeds, with complete dissolution usually being attained when about half the stoichiometric amount of phosgene has been added. It is believed that this is due to the substantially complete solubility of the spirobiindane bisphenol monochloroformate in organic liquids such as methylene chloride.

If phosgenation is continued at the relatively high pH of step A, substantial proportions of dimer and higher oligomer bischloroformates are obtained at the expense of monomer bischloroformate. This is avoided according to the present invention by continuing phosgenation in step B while decreasing the pH to a value in the range of about 2–6. At lower values within this range, substantial proportions of monochloroformate are sometimes formed, so a pH value in the range of 4–6 is preferred.

The reaction temperature in both steps is maintained in the range of about 10°–40° C. When a relatively low boiling organic liquid such as methylene chloride is employed, it is within the scope of the invention to conduct the reaction at reflux.

Under these conditions, a maximum of about 1.25 moles of phosgene per equivalent of spirobiindane bisphenol is required for complete conversion of the latter. Less phosgene, typically as little as about 1.1 moles, is frequently adequate.

The spirobiindane bisphenol bischloroformate composition is obtained as a solution in the organic liquid. Depending on the method of preparation, it may be desirable to wash said solution with a dilute aqueous acidic solution to remove traces of base used in preparation.

Following preparation of the spirobiindane bisphenol bischloroformate composition by the method of this invention, solvent may be removed and individual components of the composition, most often monomeric bisphenol bischloroformate, may be separated by conventional means such as distillation, chromatography, fractional crystallization or the like. Such operations are frequently unnecessary, however, since for many purposes, including conversion to cyclic polycarbonate oligomers, the composition may be used without solvent removal or purification.

The invention is illustrated by the following examples. Examples 3–5 are not within the scope of the invention but are presented for comparison purposes.

EXAMPLE 1

A mixture of 15.85 grams (100 meq.) of SBI, 100 ml. of methylene chloride and 10 ml. of 2.5N aqueous sodium hydroxide (25 mmol.) was heated under reflux, with stirring, as phosgene was passed in at a rate of 1 gram per minute. Phosgene passage was continued as the pH decreased; at the time it fell below 7, the solid phase in the mixture had disappeared. Sodium hydroxide solution was then added as needed to maintain the pH in the range of 2–5 as phosgene passage was continued for a total phosgene addition time of 12 minutes (121 mmol.). The aqueous and organic phases were separated and the organic phase was washed with 0.1N aqueous hydrochloric acid and filtered through phase separation paper. The bischloroformate species were converted to phenyl esters by reaction with an equimolar mixture of phenol and triethylamine and the solution was analyzed by high pressure liquid chromatography and found to contain molecular species corresponding to 43% SBI bischloroformate, 25% SBI monochloroformate and 8% SBI dimer bischloroformate.

EXAMPLE 2

The procedure was similar to that of Example 1, except that the reaction was conducted at 10° C., the initial pH was about 14 and the final pH was in the range of 4–6. This was achieved by adding approximately one half the aqueous sodium hydroxide at the beginning of the reaction, with the remainder being added as needed to maintain the stated pH. The product was found to contain 55% SBI bischloroformate, 2% SBI monochloroformate and 15% dimer bischloroformate.

EXAMPLE 3

A slurry of 31.7 grams (100 meq.) of SBI in a methylene chloride-water mixture was adjusted to a pH of 12 by the addition of 5N aqueous sodium hydroxide solution. Phosgene was bubbled into the mixture at 1 gram per minute for 25 minutes (total 253 mmol.), with stirring, as the temperature was maintained at 10° C. The reaction mixture was acidified by the addition of 3N aqueous hydrochloric acid and nitrogen was bubbled through for 1 hour. The organic phase was then separated, washed with aqueous hydrochloric acid, filtered and converted to phenyl esters as described in Example 1. Upon analysis, it was found to contain 25% SBI bischloroformate and 22% dimer bischloroformate. No SBI monochloroformate was detected.

EXAMPLE 4

The procedure was similar to that of Example 3, except that all the sodium hydroxide was added at the beginning of the reaction to provide a pH of 14. The product contained 28% SBI bischloroformate, 7% SBI monochloroformate and 15% dimer bischloroformate.

EXAMPLE 5

The procedure was similar to that of Example 3, except that the reaction mixture was maintained at a pH in the range of 2–5 for the entire reaction. Upon passage of phosgene into the mixture, the reaction mixture gelled and stirring and further phosgenation became impossible.

What is claimed is:

1. A method for preparing a composition comprising bischloroformates of spirobiindane bisphenols of the formula

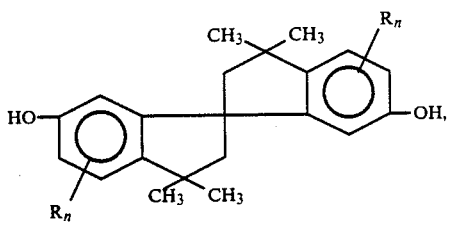

wherein each R is independently $C_{1-4}$ primary or secondary alkyl or halo and n is from 0 to 3, which comprises (A) passing phosgene into a heterogeneous mixture of said spirobiindane bisphenol, a substantially inert organic liquid and an aqueous alkali metal or alkaline earth metal base solution, said mixture being maintained at a temperature within the range of about 10°–40° C. and a pH of the aqueous phase in the range of about 8–14, until all solids have dissolved, and (B) continuing phosgene passage as the pH of the aqueous phase is decreased to a value in the range of about 2–6.

2. A method according to claim 1 wherein the pH during step A is in the range of about 12–14.

3. A method according to claim 2 wherein the organic liquid is methylene chloride.

4. A method according to claim 3 wherein the phosgene flow rate is about 0.05–3.0 moles per equivalent of spirobiindane bisphenol per minute.

5. A method according to claim 4 wherein the base is sodium hydroxide.

6. A method according to claim 5, wherein n is 0.

7. A method according to claim 1 wherein the pH is step B is in the range of 4–6.

8. A method according to claim 7 wherein the phosgene flow rate is about 0.05–3.0 moles per equivalent of spirobiindane bisphenol per minute.

9. A method according to claim 9 wherein the pH during step A is in the range of about 12–14.

10. A method according to claim 9 wherein the base is sodium hydroxide.

11. A method according to claim 10 wherein n is 0.

* * * * *